(12) United States Patent
Ella et al.

(10) Patent No.: US 8,754,043 B2
(45) Date of Patent: *Jun. 17, 2014

(54) EPIDERMAL GROWTH FACTOR COMPOSITIONS

(71) Applicants: Krishna Murthy Ella, Hyderabad (IN); Srinivas Kannappa Vellimedu, Hyderabad (IN)

(72) Inventors: Krishna Murthy Ella, Hyderabad (IN); Srinivas Kannappa Vellimedu, Hyderabad (IN)

(73) Assignee: Bharat Biotech International Limited (IN)

(*) Notice: Subject to any disclaimer, the term of this patent is extended or adjusted under 35 U.S.C. 154(b) by 0 days.

This patent is subject to a terminal disclaimer.

(21) Appl. No.: 13/912,103

(22) Filed: Jun. 6, 2013

(65) Prior Publication Data

US 2013/0272999 A1  Oct. 17, 2013

Related U.S. Application Data

(63) Continuation of application No. 11/915,727, filed as application No. PCT/IN2006/000168 on May 18, 2006, now Pat. No. 8,481,049.

(30) Foreign Application Priority Data

May 27, 2005  (IN) .............................. 642/CHE/2005

(51) Int. Cl.
*A61K 38/18* (2006.01)
*C07K 14/485* (2006.01)

(52) U.S. Cl.
USPC .......................................... 514/9.6; 530/399

(58) Field of Classification Search
CPC .............. A61K 38/1808; A61K 38/18; A61K 2300/00; A61K 9/0014
See application file for complete search history.

(56) References Cited

U.S. PATENT DOCUMENTS

| | | | |
|---|---|---|---|
| 4,803,066 A | 2/1989 | Edwards | |
| 5,427,778 A | 6/1995 | Finkenaur et al. | |
| 6,337,320 B1 | 1/2002 | Hersh et al. | |
| 6,589,540 B1 | 7/2003 | Jo | |
| 6,630,442 B1 | 10/2003 | Hersh | |
| 8,481,049 B2 * | 7/2013 | Ella et al. ................... | 424/198.1 |

FOREIGN PATENT DOCUMENTS

| | | |
|---|---|---|
| EP | 0 398 619 B1 | 8/1993 |
| FR | 2 695 556 A1 | 3/1994 |
| WO | WO 95/02411 A1 | 1/1995 |
| WO | WO 03/075949 A1 | 9/2003 |

OTHER PUBLICATIONS

PCT International Search Report and Written Opinion, PCT Application No. PCT/IN2006/000168, May 16, 2007, twelve pages.

* cited by examiner

*Primary Examiner* — Ruixiang Li
(74) *Attorney, Agent, or Firm* — Fenwick & West LLP

(57) ABSTRACT

A composition for treating a wound, wherein the composition can comprise therapeutically effective amount of an epidermal growth factor and a physiologically acceptable agent, wherein the physiologically acceptable agent comprises at least one of a stabilizer, a preservative, a thickening agent, carrier/diluent, and optionally pH regulating agent and humectant.

13 Claims, No Drawings

EPIDERMAL GROWTH FACTOR COMPOSITIONS

CROSS REFERENCE TO RELATED APPLICATIONS

This application is a continuation of U.S. patent application Ser. No. 11/915,727, filed Jun. 16, 2008, which is the National Stage of International Application No. PCT/IN2006/000168, filed May 18, 2006, and claims priority to Indian Patent Application No. 00642CHE2005, filed May 27, 2005, which are incorporated by reference herein in their entirety.

FIELD OF THE INVENTION

The invention particularly relates to a stable composition of epidermal Growth Factor (herein referred to as EGF). Particularly, the invention relates to a stable EGF composition involving novel recombinant EGF (rEGF). More particularly, the invention relates to a composition comprising an epidermal growth factor and a physiologically acceptable agent, wherein the physiologically acceptable comprises at least one of a stabilizer, a preservative and a thickening agent. Further the invention also relates to the application/use of the composition for treating wounds. The invention also describes the process for preparation of the said stable composition having rEGF as therapeutically active ingredient.

BACKGROUND OF THE INVENTION

Epidermal Growth Factor (EGF) is a single chain polypeptide having molecular weight of approximately 62 kDa and comprised of 53 amino acid residues including three disulphide bonds. Epidermal Growth Factor (EGF) is one of the most potent, biologically available entities that play a very important role in wound healing. It binds specifically to the EGF receptors present on the cell surface, thus triggering complex biochemical mechanisms in the cells to trigger the growth. EGF is biologically unstable and physiologically nonhomogenous, particularly in the presence of moisture. EGF has a short life span of about an hour whereas DNA synthesis at the site of the wound requires about eight to twelve hours. EGF exhibits loss of biological activity due to denaturation, decomposition, condensation and precipitation due to proteolytic enzymes. This is disadvantageous because such loss of activity makes it impractical to store aqueous preparations of epidermal growth factor for extended periods of time. The use of EGF formulations for wound healing is known in the art. To overcome this problem and to provide desired effective wound healing, it is reported that EGF has to be continuously applied in initial stages of healing. As a result, many formulations have been developed to increase the stability of EGF.

The prior art known to the inventors include CN 1515315 that relates to a stable synergistic composition containing EGF and bletilla extract.

U.S. Pat. No. 4,944,948 suggests a liposome gel formulation for the delivery of hEGF to the wound site to overcome the above-mentioned problems.

EP 0312208 discloses using various water-soluble or water-swellable carriers for slow release formulations for EGF. This enables release of EGF for 12 hours or more. However, these formulations are unsuitable for industrial application due to poor shelf life.

U.S. Pat. No. 4,717,717 advocates using cellulose derivative together with EGF to enhance stabilization.

EP 0312208 ('208) discloses aqueous gel formulation of EGF for controlled delivery of the active ingredient employing various water soluble polymer as a base for providing viscosity ranging from 1000 to 12,000,000 cps at room temperature.

U.S. Pat. No. 4,944,948 describes gel formulation of EGF using neutral phospholipids, negatively-charged phospholipids, and cholesterol.

Though these formulations are capable of continuously releasing EGF for 12 hours or more they are unsuitable for industrial manufacture being unstable in long term storage. Further, due to high viscosity of the formulation disclosed in '208 it forms barrier for migration of epidermal cells. Additionally, it poses problems in application at delicate wound sites.

U.S. Pat. No. 5,130,298 and EP publication No. 398615 teaches mixing EGF with metal cation for preventing degradation of EGF through ionic binding. This increases the stability of EGF to about 2 months at 4° C. This formulation also proves to be unsuitable for industrial application.

US 2003050238 advises using acidic polymer such as carboxyvinyl polymer as a base to solve the above-mentioned problems of shelf life and unsuitability for utilizing in industrial fields. The patent claims to have increased the shelf life.

PCT Application No. WO99/44631 attempts to extend shelf life of hEGF. However, none of these solutions were found successful and the stability of the enzyme remains a problem as far as it stays in aqueous environment above 0° C.

It is also noticed that EGF degrades over time to form multiple species of the EGF molecule, which are believed to be degradation products. Such degradation occurs naturally as a result of environmental factors such as light, which can cause photo-oxidation; changes in pH; changes in ionic strength; changes in temperature; and physical manipulation of the molecule. This reduces the shelf life of an EGF formulation over extended storage.

Hence, there is an imperative need to develop a stable formulation of EGF. The inventors after conducting considerable research have developed EGF composition having stability over two years while maintaining its efficacy. Further, it provides public with useful choice. After prolonged research it has been found out that the compositions of EGF particularly rEGF, when prepared using physiologically acceptable agents comprising charged protein stabilizers specifically in combination with preservative, thickening agent, pH regulating agent and a carrier proves to be stable for about 2 years.

SUMMARY OF THE INVENTION

The invention relates to a composition for treating a wound wherein the composition can comprise therapeutically effective amount of an epidermal growth factor and a physiologically acceptable agent, wherein the physiologically acceptable agent comprises at least one of a stabilizer, a preservative, a thickening agent, carrier/diluent, and optionally pH regulating agent and humectant. The stabilizer can be one of L-lysine Hydrochloride, Mannitol and carboxymethyl cellulose, the preservative can be a salt of p-hydroxy benzoic acid and the thickening agent can be polyacrylic acid. Triethanol amine being used mainly as a pH regulating agent also serves the purpose of crosslinking Humectant can be glycerol. The physiologically acceptable agent can further include alpha linolenic acid.

According to an embodiment, the composition can further comprise therapeutically effective amount of a therapeutic agent. The therapeutic agent is selected from a group consisting of a synthetic anti-infective agent, a recombinant biological active ingredient, a recombinant antibiotic, a natural product, protein free blood extract, an immune modulator, clobetasol propiate, and, a vaso constrictor.

According to another embodiment, a method for treating a wound can comprise a step of administering a composition to the wound, wherein the composition comprises therapeutically effective amount of an epidermal growth factor (EGF) and a physiologically acceptable agent, wherein the physiologically acceptable agent comprises at least one of a stabilizer, a preservative and a thickening agent.

According to another embodiment, a process of making a composition for treating a wound comprises dissolving therapeutically effective amount of a physiologically acceptable agent in water to obtain a mixture, wherein the physiologically acceptable agent comprises at least one of a stabilizer, a preservative and a thickening agent; and, adding therapeutically effective amount of an epidermal growth factor to the mixture to obtain the composition.

The composition of this invention can be formulated as semi solid form such as gel, cream, ointment for topical application, or suitable for parentaral or injectable administration by appropriately adjusting the quantities of respective responsible ingredients.

DETAILED DESCRIPTION OF THE INVENTION

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting but rather to provide an understandable description of the invention.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language).

The present invention relates to a composition for treating a wound. According to one embodiment, the composition comprises therapeutically effective amounts of an epidermal growth factor and a physiologically acceptable agent, wherein the physiologically acceptable agent comprises at least one of a stabilizer, a preservative a thickening agent, carrier/diluent, and optionally pH regulating agent and humectant. According to an embodiment, the epidermal growth factor can be a recombinant epidermal growth factor. The epidermal growth factor can be in the range of about 0.001% to about 0.1% (w/w).

According to an embodiment, the stabilizer comprises one of L-lysine Hydrochloric acid, mannitol and carboxymethylcellulose, the preservative comprises a salt of p-hydroxy benzoic acid and the thickening agent comprises polyacrylic acid. According to a further embodiment, the preservative comprises sodium methyl paraben and sodium propyl paraben. The physiologically acceptable agent also includes components, in addition to the epidermal growth factor, which are suitable for administration to the patient being treated in accordance with the invention. For example, the physiologically acceptable agent can include components, which result in a stable composition or increase the efficacy of the composition. According to another embodiment, the physiologically acceptable agent further comprise water, triethanolamine, alpha linolenic acid, and glycerol. The mannitol can be in the range of about 0.5% to about 10% w/w. The L-lysine hydrochloric acid can be in the range of about 0.1% to about 2% w/w. The polyacrylic acid can be in the range of about 0.25% to about 3% w/w. The triethanolamine can be in the range of about 1% to about 20% (w/w). The sodium methyl paraben can be about 0.016% to about 0.18% (w/w) and the sodium propyl paraben can be about 0.01% to about 0.02% (w/w). The glycerol can be about 1.0% to about 2.5% (w/w) and the carboxymethylcellulose can be in the range of about 0.6% to about 1.6% (w/w). The water can be in the range of about 50% to about 95% (w/v).

According to another embodiment, the composition can further comprise water of about 98% (w/v), wherein the polyacrylic acid is in the range of about 0.25% to about 0.8% (w/w), triethanolamine is in the range of about 1% to about 20% (v/v), sodium methyl paraben is about 0.18% w/w and sodium propyl paraben is about 0.02% (w/w). The composition can be formulated as a semi-solid drug delivery formulation.

According to another embodiment, the composition can further comprise water of about 97.5% to about 99% w/v, wherein the carboxymethylcellulose is in the range of about 0.6% to about 1.6% (w/w). The composition can be formulated as a capsule.

According to another embodiment, the composition can further comprise therapeutically effective amount of a therapeutic agent. According to an embodiment, the therapeutic agent can include components, which can assist in the wound-healing process and are suitable for administration to patients. The therapeutic agent can also include components, which perform additional functions such as increasing the uptake of oxygen, moisturizing or increasing the proliferation of granulocytes or macrophages, etc. The therapeutic agent can include components which perform functions in addition to those performed by the epidermal growth factor. The therapeutic agent can be selected from a group consisting of a synthetic anti-infective agent, a recombinant biological active ingredient, a recombinant antibiotic, a natural product, protein free blood extract, an immune modulator, clobetasol propiate, and, a vaso constrictor.

According to an embodiment, the synthetic anti-infective agent may be selected from a synthetic group comprising erythromycin, mupricin, soframycin, clindamycin phosphate, fluconazole and silver sulphadiazine. The synthetic anti-infective agent can be in the range of about 0.1% to about 5% (w/w). According to another embodiment, the synthetic anti-infective agent can comprise silver sulphadiazine in the range of about 0.05% to about 0.5% (w/w).

According to an embodiment, the biological active can be selected from a biological group consisting of hyaluronic acid, a granulocyte colony stimulating factor, and a transforming growth factor-alpha. Hyaluronic acid (HA) is found extensively in nature in micro organisms, in humans and also in animals. It is highly viscous lubricant and hence can be used as a moisturizer. According to an embodiment, hyaluronic acid can be used in combination with EGF for reendothelialization in the anterior chamber of the eye. The hyaluronic acid can be in the range of about 0.1% to about 5% (w/v). The Granulocyte macrophage-colony stimulating factor (GM-CSF) increases the proliferation of granulocytes and macrophages. The granulocyte colony stimulating factor can be in the range of about 0.002% to about 0.004% (w/w). The Transforming Growth Factor-Alpha promotes normal wound healing through a concerted effort with Epidermal Growth Factor and Platelet-Derived Growth Factor (PDGF). The transforming growth factor-alpha can be in the range of about 0.001% to about 0.1% (w/w).

According to an embodiment, the recombinant antibiotic comprises lysostaphin. Lysostaphin is a biological antibiotic produced by Staphylococcus. Lysostaphin can be cloned and expressed in *E. Coli*, and purified and formulated at suitable concentration to give antibacterial effects in combination with EGF at therapeutically effective concentration. The lysostaphin can be in the range of about 0.001% to about 0.1% (w/w).

According to another embodiment, the natural product can be selected from the group which can comprise aloe vera, honey, turmeric and sandal wood. Turmeric is an excellent natural antibiotic. The aloe vera can be in the range of about 1% to about 2% (w/w), the honey can be in the range of about 0.1% to about 1% (w/w), the turmeric can be in the range of about 5% to about 80% (w/w) and the sandal wood can be in the range of about 0.2% to about 1% (w/w).

According to another embodiment, the composition can comprise the protein free blood extract in the range of about 0.02% (w/w). Protein free blood extract improves the utilization of oxygen and promotes the uptake of nutrients into the cell.

According to an embodiment, the immune modulator comprises beta-1,3-D-glucan. The composition can further comprise an effective amount of vitamin A, vitamin C and vitamin D, wherein the immune modulator comprises beta-1,3-D-glucan in the range of about 0.5% to about 2% (w/w). Beta-1,3-D-glucan itself can elicit broad anti-infective effects such as antibody response against *Staphylococcus aureus, Escherichia coil, Candida albicans, Pneumocytis carinii, Listeria monococytogenesis, Leishmania donovani*, and Herpes simplex.

According to an embodiment, the vaso constrictor comprises hydrocortisone acetate. The composition can further comprise lidocaine in the range of about 2% to about 5% (w/w), zinc oxide in the range of about 2% to about 5% (w/w), allantoin in the range of about 0.25% to about 2.5% (w/w), wherein the vaso constrictor comprises hydrocortisone acetate in the range of about 0.15% to about 0.25% (w/w). According to an embodiment, the composition can be used in treating hemorrhoids and fissure proctitis. The composition can also provide symptomatic pain relief.

According to an embodiment, the composition can further comprise zinc oxide in the range of about 2% to about 5% (w/w) and salicylic acid in the range of about 0.1% to about 5% (w/w), wherein the therapeutic agent comprises clobetasol propionate in the range of about 0.1% to about 1% (w/w).

According to another embodiment, the composition can be formulated as a topical formulation. The topical formulation is selected from a group comprising gels, sprays, ointments, creams and lotions. According to an embodiment, the composition can also be as an oral formulation suitable for oral administration and a parenteral formulation suitable for parenteral administration. The formulations for oral administration can comprise capsules. The formulations for parenteral administration can include injections. However, the scope of the invention is not just limited to these formulation types but can also be expanded to other formulation types known to those skilled in the art.

According to another embodiment, a method for treating a wound can comprise a step of administering an effective amount of the composition, wherein the composition comprises therapeutically effective amount of an epidermal growth factor and a physiologically acceptable agent, wherein the physiologically acceptable agent comprises at least one of a stabilizer, a preservative, a thickening agent, carrier/diluent, and optionally pH regulating agent and humectant. According to an embodiment, the stabilizer comprises one of L-lysine Hydrochloric acid, mannitol, and carboxymethylcellulose, the preservative comprises a salt of p-hydroxy benzoic acid and the thickening agent comprises polyacrylic acid. According to a further embodiment, the preservative comprises sodium methyl paraben and sodium propyl paraben. According to another embodiment, the physiologically acceptable agent can further comprise water as carrier, triethanolamine, alpha linolenic acid, and glycerol (humectant).

According to another embodiment, the composition can further comprise therapeutically effective amounts of a therapeutic agent. The therapeutic agent can be selected from a group comprising a synthetic anti-infective agent, a recombinant biological active ingredient, a recombinant antibiotic, a natural product, protein free blood extract, an immune modulator, clobetasol propiate, silver sulphadiazine and a vaso constrictor.

According to another embodiment, the composition can be used in treating wounds such as ulcers, for example, diabetic foot ulcer, corneal ulcer, gastric ulcer, venous ulcer, arterial ulcer and pressure ulcer, skin burns caused by irradiation used in cancer therapy, sports injury, thermal injury, chemical injury, physical injury, osteomyelitis, dermatitis, muscle soreness, joint soreness, muscle stiffness, joint stiffness, laceration, scarring, surgical wound, bedsores and cuts due to environmental factors, marks due to childbirth, loss of sensation due to *Mycobacterium leprae* infection or by infections which cause similar conditions, hemorrhoids and gastro duodenal ulcer, growth of hair follicles, and in all other skin ailments which need to be repaired.

According to another embodiment, a process of preparing a composition for treating a wound is provided. The process can comprise initially dissolving therapeutically effective amount of a physiologically acceptable agent in water to obtain a mixture, wherein the physiologically acceptable agent comprises at least one of a stabilizer, a preservative and a thickening agent. According to an embodiment, the stabilizer comprises one of L-lysine Hydrochloric acid and carboxymethylcellulose, the preservative comprises a salt of p-hydroxy benzoic acid and the thickening agent comprises polyacrylic acid. According to a further embodiment, the preservative comprises sodium methyl paraben and sodium propyl paraben. The process can further comprise adding therapeutically effective amount of an epidermal growth factor to the mixture to obtain the composition for treating the wound.

According to another embodiment, the process can further comprise adding therapeutically effective amounts of at least one of L-lysine hydrochloric acid, mannitol and polyacrylic acid to the mixture to obtain a suspension. A therapeutically effective amount of glycerol can be added to this suspension. The suspension can be stirred so as to allow it to swell. The pH of the suspension can be maintained at about 6.3 to 6.4. The pH of the suspension can be maintained by the addition of triethanolamine to the suspension.

According to another embodiment, the process can also further comprise adding therapeutically effective amount of a therapeutic agent to the composition. The therapeutic agent can be selected from a group comprising a synthetic anti-infective agent, a biological active, a recombinant antibiotic, a natural product, protein free blood extract, an immune modulator, clobetasol propiate and a vaso constrictor. The synthetic anti-infective agent can be selected from a synthetic group comprising erythromycin, mupricin, soframycin, clindamycin phosphate, fluconazole and silver sulphadiazine, the biological active can be selected from a biological group consisting of hyaluronic acid, a granulocyte colony stimulating factor, and a transforming growth factor-alpha, the recombinant antibiotic comprises lysostaphin, the natural product can be selected from the group consisting aloe vera, honey, turmeric and sandal wood, the immune modulator comprises beta-1,3-D-glucan, and the vaso constrictor comprises hydrocortisone acetate.

The composition for treating a wound is described with reference to the following examples. Percentages in the examples are stated as a percentage of the total composition. These examples are provided as an illustration of the invention and are not intended to limit the scope of the invention.

Example 1

A mixture was obtained by dissolving about 0.165% of sodium methyl paraben and about 0.018% sodium propyl paraben in purified water of about 91.57%. Subsequently, about 0.458% of L-lysine hydrochloride, about 4.579% of mannitol and about 0.916% polyacrylic acid were added to the mixture to obtain a suspension. The suspension was further allowed to swell by stirring. An effective amount of glycerol of about 2.289% was added to this suspension. The pH was maintained at about 6.3 to 6.4 with the addition of effective amount of triethanolamine. Finally, a therapeutically effective amount of EGF of about 0.005% was added to obtain the composition for treating the wound.

Example 2

A mixture was obtained by dissolving about 0.162% of sodium methyl paraben and about 0.018% sodium propyl paraben in purified water of about 89.916%. Subsequently, about 0.450% of L-lysine hydrochloride, about 4.496% of mannitol and about 2.697% polyacrylic acid were added to the mixture to obtain a suspension. The suspension was further allowed to swell by stirring. An effective amount of glycerol of about 2.248% was added to this suspension. The pH was maintained at about 6.3 to 6.4 with the addition of effective amount of triethanolamine. Finally, a therapeutically effective amount of EGF of about 0.013% was added to obtain the composition for treating the wound.

Example 3

A mixture was obtained by dissolving about 0.157% of sodium methyl paraben and about 0.017% sodium propyl paraben in purified water of about 87.497%. Subsequently, about 0.437% of L-lysine hydrochloride, about 8.750% of mannitol and about 0.875% polyacrylic acid were added to the mixture to obtain a suspension. The suspension was further allowed to swell by stirring. An effective amount of glycerol of about 2.187% was added to this suspension. The pH was maintained at about 6.3 to 6.4 with the addition of effective amount of triethanolamine. Finally a therapeutically effective amount of EGF of about 0.079% was added to obtain the composition for treating the wound.

Various combinations of EGF were thus carried out and the combinations were subjected to thermal stability as per ICH guidelines. Pre-clinical studies for safety of the formulations with varying percentages of EGF, were conducted in both rats and rabbits, as per the approved guidelines. Briefly, acute toxicity studies were carried out for 8 days, sub-acute studies were carried on for 30 days and ocular irritation study was conducted for 7 days.

Results indicated that the animals were normal during the study and none of the animals showed any signs of toxicity related to general behavior, central and autonomic nervous system, respiratory and circulatory system. The wound region was devoid of bleeding and erythema through the period of study.

The growth rate and food consumption in control and treated animals were normal & did not differ significantly. The biochemical parameters studied in control and treated groups were within the normal range and no abnormality was observed. The statistical evaluation revealed that the differences observed between the control and the different treatment groups were not statistically indicating that rh EGF has not influenced any of the parameters studied. There were no observable changes in the hematological parameters between the control and treated groups.

There was no observable anti-body response in the treated groups with EGF, in both rats and rabbits. The protein content in the control and the treated groups did not differ significantly in both the species studied. The collagen content was significantly increased in medium and high dosage groups in males and females of both the species on the 15th and the 31st days.

Subsequently, the formulation was also tested in patients suffering from donor site skin grafts, burns and diabetic foot ulcers.

Data revealed that the healing time for donor site skin graft in the test group was 7 days in comparison to the control, which was 13 days ($P<0.001$). In treatment with burns cases, the healing time was 9 days in the test group while in the control it was observed to be 20 days ($P<0.05$).

The healing rate in diabetic foot was compared at 7 weeks and 15 weeks. It was found that by 7 weeks, 6.25% of the control cases were healed, while in the treated group 56% cases were healed. The value of $P<0.001$ states the above significance. It was observed that by 15 weeks, 37.5% of the control cases were healed, while in the test group 88% cases were healed. The value of $P<0.005$ states the above significance.

The stability of EGF in the gel form has been conducted in both real time ($5+/-3°$ C.) and accelerated time ($25+/-2$ and 60% RH+/−5%). The stability of the formulation was monitored for 2 years at real time and for 6 months at accelerated time. Data indicated that the molecule was stable and showed no significant drop in activity during the period of study.

The present study was carried out in wounds, which are more than 20 $cms^2$, and about 10-40 mm in depth.

The scope of the combination is not limited just by the above range, but also to other combinations, which can still maintain the same functional activity of EGF known to those who are skilled in the art. This combination is used as curative for skin grafts, burns, cuts, diabetic foot ulcer, post operative wounds, bed sores, vitiligo and repair of skin damage caused by irradiation leading to cancer.

Example 4

A mixture was obtained by dissolving sodium methyl paraben of about 0.163% and sodium propyl paraben of about 0.018% in purified water of about 90.739%. Subsequently about 0.454% of L-lysine hydrochloride, about 4.537% of mannitol and about 0.907% of polyacrylic acid were added to the mixture to obtain a suspension. The suspension was further allowed to swell by stirring. An effective amount of glycerol of about 2.268% was added to the suspension. The pH was maintained at about 6.3 to 6.4 with the addition of effective amount of triethanolamine. Finally therapeutically effective amount of the antibiotic infective agent of about 0.907% and the epidermal growth factor (EGF) about 0.005% was added to obtain the composition for treating the wound.

Example 5

A mixture was obtained by dissolving sodium methyl paraben of about 0.016% and sodium propyl paraben of about 0.018% in purified water of about 90.803%. Subsequently about 0.453% of L-lysine hydrochloride, about 4.540% of mannitol and about 0.908% of polyacrylic acid were added to the mixture to obtain a suspension. The suspension was further allowed to swell by stirring. An effective amount of glycerol of about 2.270% was added to the suspension. The pH was maintained at about 6.3 to 6.4 with the addition of effective amount of triethanolamine. Finally therapeutically effective amount of the antibiotic infective agent of about 0.908% and the epidermal growth factor (EGF) about 0.082% were added to obtain the composition for treating the wound.

Example 6

A mixture was obtained by dissolving about 0.164% sodium methyl paraben and about 0.018% sodium propyl paraben in purified water of about 91.478%. Subsequently L-lysine hydrochloride of about 0.457%, mannitol of about 4.574% and polyacrylic acid of about 0.914% were added to the mixture to obtain a suspension. The suspension was further allowed to swell by stirring. To this suspension, effective amount of glycerol of about 2.286% was added. The pH was maintained at about 6.3 to 6.4 with the addition of effective amount of triethanolamine. Finally therapeutically effective amount of hyaluronic acid of about 0.091%, followed by therapeutically effective amount of the epidermal growth factor (EGF) of about 0.014% was added to obtain the composition for treating the wound.

Example 7

A mixture was obtained by dissolving about 0.158% sodium methyl paraben and about 0.017% sodium propyl paraben in purified water of about 88.269%. Subsequently L-lysine hydrochloride of about 0.441%, mannitol of about 4.413% and polyacrylic acid of about 0.882% were added to the mixture to obtain a suspension. The suspension was further allowed to swell by stirring. To this suspension, effective amount of glycerol of about 2.206% was added. The pH was maintained at about 6.3 to 6.4 with the addition of effective amount of triethanolamine. Finally therapeutically effective amount of hyaluronic acid of about 3.530%, followed by therapeutically effective amount of the epidermal growth factor (EGF) of about 0.079% was added to obtain the composition for treating the wound.

Example 8

A mixture was obtained by dissolving about 0.165% of sodium methyl paraben and about 0.018% of sodium propyl paraben in purified water of about 91.521%. Subsequently L-lysine hydrochloride of about 0.458%, mannitol of about 4.576% and polyacrylic acid of about 0.915% were added to the mixture to obtain a suspension. The suspension was further allowed to swell by stirring. To this suspension effective amount of glycerol of about 2.288% was added. The pH was maintained at about 6.3 to 6.4 with the addition of effective amount of triethanolamine. Finally therapeutically effective amount of epidermal growth factor (EGF) of about 0.014% followed by Lysostaphin in therapeutically effective amount of about 0.046% was added to obtain the composition for treating the wound.

Example 9

A mixture was obtained by dissolving about 0.164% of sodium methyl paraben and about 0.018% of sodium propyl paraben in purified water of about 91.424%. Subsequently L-lysine hydrochloride of about 0.457%, mannitol of about 4.570% and polyacrylic acid of about 0.914% were added to the mixture to obtain a suspension. The suspension was further allowed to swell by stirring. To this suspension effective amount of glycerol of about 2.285% was added. The pH was maintained at about 6.3 to 6.4 with the addition of effective amount of triethanolamine. Finally, therapeutically effective amount of epidermal growth factor (EGF) of about 0.082% followed by Lysostaphin in therapeutically effective amount of about 0.082% was added to obtain the composition for treating the wound.

Example 10

A mixture was obtained by dissolving about 0.162 of sodium methyl paraben and 0.018% of sodium propyl paraben in purified water of about 90.232%. Subsequently, about 0.451% of L-lysine hydrochloride, about 4.512% of mannitol and 0.902% of polyacrylic acid in were added to the mixture to obtain a suspension. The suspension was further allowed to swell by stirring. To this suspension effective amount of glycerol of about 2.256% was added. The pH was maintained at about 6.3 to 6.4 with the addition of effective amount of triethanolamine. Finally, therapeutically effective amount of epidermal growth factor (EGF) of about 0.005%, followed by effective amounts of aloe vera of about 0.902%, vitamin E of about 0.541% and vitamin C of about 0.018% were added to obtain the composition for treating the wound.

Example 11

A mixture was obtained by dissolving about 0.154% of sodium methyl paraben and 0.017% of sodium propyl paraben in purified water of about 85.752%. Subsequently, about 0.429% of L-lysine hydrochloride, about 4.288% of mannitol and 0.858% of polyacrylic acid in were added to the mixture to obtain a suspension. The suspension was further allowed to swell by stirring. To this suspension effective amount of glycerol of about 2.144% was added. The pH was maintained at about 6.3 to 6.4 with the addition of effective amount of triethanolamine. Finally, therapeutically effective amount of epidermal growth factor (EGF) of about 0.013%, followed by effective amounts of aloe vera of about 5.145%, vitamin E of about 0.858% and vitamin C of about 0.343% were added to obtain the composition for treating the wound.

Example 12

A mixture was obtained by dissolving about 0.147% of sodium methyl paraben and 0.016% of sodium propyl paraben in purified water of about 81.907%. Subsequently, about 0.410% of L-lysine hydrochloride, about 4.095% of mannitol and 0.819% of polyacrylic acid in were added to the mixture to obtain a suspension. The suspension was further allowed to swell by stirring. To this suspension effective amount of glycerol of about 2.048% was added. The pH was maintained at about 6.3 to 6.4 with the addition of effective amount of triethanolamine. Finally therapeutically effective amount of epidermal growth factor (EGF) of about 0.074%, followed by effective amounts of aloe vera of about 8.191%, vitamin E of about 1.474% and vitamin C of about 0.819% were added to obtain the composition for treating the wound.

Example 13

A mixture was obtained by dissolving about 0.149% of sodium methyl paraben and about 0.017% of sodium propyl paraben in purified water of about 82.757%. Subsequently about 0.414% of L-lysine hydrochloride, about 4.138% of mannitol and about 0.828% of polyacrylic acid in effective amounts were added to the mixture to obtain a suspension. The suspension was further allowed to swell by stirring. To this suspension effective amount of glycerol of about 2.069% was added. The pH was maintained at about 6.3 to 6.4 with the addition of effective amount of triethanolamine. Finally, therapeutically effective amount of epidermal growth factor (EGF) of 0.005%, followed by effective amounts of aloe vera of about 0.828%, turmeric of about 8.276%, sandal wood of about 0.248% and honey of about 0.273% were added to obtain the composition for treating the wound.

Example 14

A mixture was obtained by dissolving about 0.098% of sodium methyl paraben and about 0.011% of sodium propyl paraben in purified water of about 54.478%. Subsequently about 0.273% of L-lysine hydrochloride, about 2.734% of mannitol and about 0.547% of polyacrylic acid in effective amounts were added to the mixture to obtain a suspension. The suspension was further allowed to swell by stirring. To this suspension effective amount of glycerol of about 1.367% was added. The pH was maintained at about 6.3 to 6.4 with the addition of effective amount of triethanolamine. Finally, therapeutically effective amount of epidermal growth factor (EGF) of about 0.049%, followed by effective amounts of aloe vera of about 0.984%, turmeric of about 38.274%, sandal wood of about 0.492% and honey of about 0.492% were added to obtain the composition for treating the wound.

Example 15

A mixture was obtained by dissolving about 0.164% of sodium methyl paraben and about 0.018% of sodium propyl paraben in purified water of about 91.553%. Subsequently L-lysine hydrochloride of about 0.457%, mannitol of about 4.577% and polyacrylic acid of about 0.915% in were added to the mixture to obtain a suspension. The suspension was further allowed to swell by stirring. To this suspension effective amount of glycerol of about 2.288% was added. The pH was maintained at about 6.3 to 6.4 with the addition of effective amount of triethanolamine. Finally, therapeutically effective amount of epidermal growth factor (EGF) about 0.010% followed by effective amount of the protein free blood extract of about 0.018% were added to obtain the composition for treating the wound.

Example 16

A mixture was obtained by dissolving about 0.165% of sodium methyl paraben and about 0.018% of sodium propyl paraben in purified water of about 91.483%. Subsequently L-lysine hydrochloride of about 0.457%, mannitol of about 4.574% and polyacrylic acid of about 0.915% in were added to the mixture to obtain a suspension. The suspension was further allowed to swell by stirring. To this suspension effective amount of glycerol of about 2.287% was added. The pH was maintained at about 6.3 to 6.4 with the addition of effective amount of triethanolamine. Finally, therapeutically effective amount of epidermal growth factor (EGF) about 0.082% followed by effective amount of the protein free blood extract of about 0.018% were added to obtain the composition for treating the wound.

Example 17

A mixture was obtained by dissolving about 0.165% of sodium methyl paraben and 0.018% of sodium propyl paraben in purified water of about 91.560%. Subsequently L-lysine hydrochloride of about 0.458%, mannitol of about 4.578% and polyacrylic acid of about 0.916% were added to the mixture to obtain a suspension. The suspension was further allowed to swell by stirring. To this suspension effective amount of glycerol of about 2.289% was added. The pH was maintained at about 6.3 to 6.4 with the addition of effective amount of triethanolamine. Finally, therapeutically effective amount of epidermal growth factor (EGF) of about 0.014% followed by effective amount of GM-CSF of about 0.003% were added to obtain the composition for treating the wound.

Example 18

A mixture was obtained by dissolving about 0.165% of sodium methyl paraben and 0.018% of sodium propyl paraben in purified water of about 91.496%. Subsequently L-lysine hydrochloride of about 0.457%, mannitol of about 4.574% and polyacrylic acid of about 0.914% were added to the mixture to obtain a suspension. The suspension was further allowed to swell by stirring. To this suspension effective amount of glycerol of about 2.287% was added. The pH was maintained at about 6.3 to 6.4 with the addition of effective amount of triethanolamine. Finally, therapeutically effective amount of epidermal growth factor (EGF) of about 0.082% followed by effective amount of GM-CSF of about 0.003% were added to obtain the composition for treating the wound.

Example 19

A mixture was obtained by dissolving about 0.164% of sodium methyl paraben and about 0.018% of sodium propyl paraben in purified water of about 90.567%. Subsequently L-lysine hydrochloride of about 0.460%, mannitol of about 4.550% and polyacrylic acid of about 0.910% were added to the mixture to obtain a suspension. The suspension was further allowed to swell by stirring. To this suspension effective amount of glycerol of about 2.270% was added. The pH was maintained at about 6.3 to 6.4 with the addition of effective amount of triethanolamine. Finally, therapeutically effective amount of epidermal growth factor (EGF) of about 0.010% followed by effective amounts of Beta-1,3-D-glucan of about 0.550%, were added to obtain the composition for treating the wound.

Example 20

A mixture was obtained by dissolving about 0.163% of sodium methyl paraben and about 0.018% of sodium propyl paraben in purified water of about 90.567%. Subsequently L-lysine hydrochloride of about 0.453%, mannitol of about 4.528% and polyacrylic acid of about 0.906% were added to the mixture to obtain a suspension. The suspension was further allowed to swell by stirring. To this suspension effective amount of glycerol of about 2.264% was added. The pH was maintained at about 6.3 to 6.4 with the addition of effective amount of triethanolamine. Finally, therapeutically effective amount of epidermal growth factor (EGF) of about 0.014% followed by effective amounts of Beta-1,3-D-glucan of about 1.087%, were added to obtain the composition for treating the wound.

Example 21

A mixture was obtained by dissolving about 0.165% of sodium methyl paraben and about 0.018% sodium propyl paraben in purified water of about 91.565%. Subsequently L-lysine hydrochloride of about 0.458%, mannitol of about 4.578% and polyacrylic acid of about 0.916% were added to the mixture to obtain a suspension. The suspension was further allowed to swell by stirring. To this suspension effective amount of glycerol of about 2.289% was added. The pH was maintained at about 6.3 to 6.4 with the addition of effective amount of triethanolamine. Finally, therapeutically effective amount of epidermal growth factor (EGF) of about 0.005% followed by effective amount of PDGF of about 0.005% were added to obtain the composition for treating the wound.

Example 22

A mixture was obtained by dissolving about 0.165% of sodium methyl paraben and about 0.018% sodium propyl paraben in purified water of 91.424%. Subsequently L-lysine hydrochloride of about 0.457%, mannitol of about 4.571% and polyacrylic acid of about 0.914% were added to the mixture to obtain a suspension. The suspension was further allowed to swell by stirring. To this suspension effective amount of glycerol of about 2.286 was added. The pH was maintained at about 6.3 to 6.4 with the addition of effective amount of triethanolamine. Finally, therapeutically effective amount of epidermal growth factor (EGF) 0.082% followed by effective amount of PDGF of about 0.082% were added to obtain the composition for treating the wound.

Example 23

A mixture was obtained by dissolving about 0.164% of sodium methyl paraben and about 0.018% of sodium propyl paraben in purified water of about 91.286%. Subsequently L-lysine hydrochloride of about 0.456%, mannitol of about 4.564%, polyacrylic acid of about 0.913%, zinc oxide of about 0.018%, salicyclic acid of about 0.018%, clobetasol propioate of about 0.274% were added to the mixture to obtain a suspension. The suspension was further allowed to swell by stirring. To this suspension effective amount of glycerol of about 2.282% was added. The pH was maintained at about 6.3 to 6.4 with the addition of effective amount of triethanolamine. Finally, a therapeutically effective amount of epidermal growth factor (EGF) of about 0.005% was added to obtain the composition for treating the wound.

Example 24

A mixture was obtained by dissolving about 0.157% of sodium methyl paraben and about 0.017% of sodium propyl paraben in purified water of about 87.478%. Subsequently L-lysine hydrochloride of about 0.437%, mannitol of about 4.374%, polyacrylic acid of about 0.876%, zinc oxide of about 2.187%, salicyclic acid of about 1.750%, clobetasol propionate of about 0.525% were added to the mixture to obtain a suspension. The suspension was further allowed to swell by stirring. To this suspension, effective amount of glycerol of about 2.187% was added. The pH was maintained at about 6.3 to 6.4 with the addition of effective amount of triethanolamine. Finally, a therapeutically effective amount of epidermal growth factor (EGF) of about 0.013% was added to obtain the composition for treating the wound.

Example 25

A mixture was obtained by dissolving about 0.152% of sodium methyl paraben and about 0.017% of sodium propyl paraben in of purified water of about 84.610. Subsequently L-lysine hydrochloride of about 0.423%, mannitol of about 4.230%, polyacrylic acid of about 0.846%, zinc oxide of about 3.384%, salicyclic acid of about 3.384%, clobetasol propionate of about 0.761% were added to the mixture to obtain a suspension. The suspension was further allowed to swell by stirring. To this suspension effective amount of glycerol of about 2.115% was added. The pH was maintained at about 6.3 to 6.4 with the addition of effective amount of triethanolamine. Finally, a therapeutically effective amount of epidermal growth factor (EGF) of about 0.076% was added to obtain the composition for treating the wound.

Example 26

A mixture was obtained by dissolving about 0.164% of sodium methyl paraben and about 0.018% of sodium propyl paraben in of purified water of about 91.490%. Subsequently L-lysine hydrochloride of about 0.457%, about 4.570% of mannitol and about 0.914% of polyacrylic acid were added to the mixture to obtain a suspension. The suspension was further allowed to swell by stirring. To this suspension effective amount of glycerol of about 2.287% was added. The pH was maintained at about 6.3 to 6.4 with the addition of triethanolamine. Finally, therapeutically effective amounts of epidermal growth factor (EGF) of about 0.010% followed by effective amount of silver sulphadiazine of about 0.091% were added to obtain the composition for treating the wound.

Example 27

A mixture was obtained by dissolving about 0.16% of sodium methyl paraben and about 0.020% of sodium propyl paraben in of purified water of about 91.360%. Subsequently L-lysine hydrochloride of about 0.46%, about 4.570% of mannitol and about 0.910% of polyacrylic acid were added to the mixture to obtain a suspension. The suspension was further allowed to swell by stirring. To this suspension effective amount of glycerol of about 2.280% was added. The pH was maintained at about 6.3 to 6.4 with the addition of triethanolamine. Finally, therapeutically effective amount of epidermal growth factor (EGF) of about 0.010% followed by effective amount of silver sulphadiazine of about 0.230% were added to obtain the composition for treating the wound.

Example 28

A mixture was obtained by dissolving about 0.164% of sodium methyl paraben and about 0.018% of sodium propyl paraben in purified water of about 91.228%. Subsequently L-lysine hydrochloride of about 0.456%, about 4.561% of mannitol and about 0.912% of polyacrylic acid were added to the mixture to obtain a suspension. The suspension was further allowed to swell by stirring. To this suspension effective amount of glycerol of about 2.281% was added. The pH was maintained at about 6.3 to 6.4 with the addition of triethanolamine. Finally, therapeutically effective amount of epidermal growth factor (EGF) of about 0.014% followed by effective amount of silver sulphadiazine of about 0.365% were added to obtain the composition for treating the wound.

Example 29

A mixture was obtained by dissolving about 0.155% of sodium methyl paraben and about 0.017% of sodium propyl paraben in purified water of about 85.873%. Subsequently L-lysine hydrochloride of about 0.429%, mannitol of about 4.294% and polyacrylic acid of about 0.859% were added to the mixture to obtain a suspension. The suspension was further allowed to swell by stirring. To this suspension effective amount of glycerol of about 2.147% was added. The pH was maintained at about 6.3 to 6.4 with the addition of triethanolamine. Finally therapeutically effective amounts of epidermal growth factor (EGF) of about 0.001%, followed by effective amounts of hydrocortisone acetate of about 0.215%, lidocaine of about 2.147%, zinc oxide of about 3.435%, and allantoin of about 0.429% to obtain the composition for treating the wound.

Example 30

A mixture was obtained by dissolving about 0.155% of sodium methyl paraben and about 0.017% of sodium propyl paraben in purified water of about 85.859%. Subsequently L-lysine hydrochloride of about 0.429%, mannitol of about 4.293% and polyacrylic acid of about 0.859% were added to the mixture to obtain a suspension. The suspension was further allowed to swell by stirring. To this suspension effective amount of glycerol of about 2.147% was added. The pH was maintained at about 6.3 to 6.4 with the addition of triethanolamine. Finally, therapeutically effective amount of epidermal growth factor (EGF) of about 0.005%, followed by effective amounts of hydrocortisone acetate of about 0.215%, lidocaine of about 2.147%, zinc oxide of about 3.435%, and allantoin of about 0.429% to obtain the composition for treating the wound.

Example 31

A mixture was obtained by dissolving about 0.151% of sodium methyl paraben and about 0.017% of sodium propyl paraben in purified water of about 83.742%. Subsequently L-lysine hydrochloride of about 0.419%, mannitol of about 4.187% and polyacrylic acid of about 0.837% were added to the mixture to obtain a suspension. The suspension was further allowed to swell by stirring. To this suspension effective amount of glycerol of about 2.094% was added. The pH was maintained at about 6.3 to 6.4 with the addition of triethanolamine. Finally therapeutically effective amounts of epidermal growth factor (EGF) of about 0.013%, followed by effective amounts of hydrocortisone acetate of about 0.167%, lidocaine of about 2.931%, zinc oxide of about 4.187%, and allantoin of about 1.256% to obtain the composition for treating the wound.

Example 32

A mixture was obtained by dissolving about 0.179% of sodium methyl paraben and about 0.020% of sodium propyl paraben in purified water of about 99.034%. Subsequently L-lysine hydrochloride of about 0.419%, and polyacrylic acid in effective amount of about 0.249% was added to the mixture to obtain a suspension. The suspension was further allowed to swell by stirring. The pH was maintained at about 6.3 to 6.4 with the addition of triethanolamine. Finally, a therapeutically effective amount of epidermal growth factor (EGF) in the range of about 0.099% was added to obtain the composition for treating the wound.

Example 33

A mixture was obtained by dissolving about 0.177% of sodium methyl paraben and about 0.020% of sodium propyl paraben in purified water of about 97.765%. Subsequently, L-lysine hydrochloride of about 0.419%, and polyacrylic acid in effective amount of about 0.736% was added to the mixture to obtain a suspension. The suspension was further allowed to swell by stirring. The pH was maintained at about 6.3 to 6.4 with the addition of triethanolamine. Finally, a therapeutically effective amount of epidermal growth factor (EGF) in the range of about 0.884% was added to obtain the composition for treating the wound.

Example 34

An effective amount of purified water of about 98.131% was initially heated to 80 degree C. To this water, effective amount of carboxymethylcellulose of about 1% was added and the mixture was allowed to swell by stirring. The mixture obtained was sterilized at 121 degree C. for 15 minutes. The sterilized mixture was then allowed to cool. Subsequently L-lysine hydrochloride of about 0.419% was added. Finally, therapeutically effective amount of epidermal growth factor (EGF) of about 0.45% was added and allowed to mix thoroughly to obtain the composition for treating the wound.

Example 35

An effective amount of purified water of about 97.381% was initially heated to 80 degree C. To this water, effective amount of carboxymethylcellulose of about 1.64% was added and the mixture was allowed to swell by stirring. The mixture obtained was sterilized at 121 degree C. for 15 minutes. The sterilized mixture was then allowed to cool. Subsequently L-lysine hydrochloride of about 0.419% was added. Finally, therapeutically effective amounts of epidermal growth factor (EGF) of about 0.9% was added and allowed to mix thoroughly to obtain the composition for treating the wound.

The process of addition of the ingredients can be carried out in the same sequence or in different sequences, which can give the same stable formulation known to those experienced in the art of formulations. The scope of the invention is not limited to the addition of same excipients or other excipients having similar functions or different concentrations in the same sequence but also to other addition sequences which can give stable formulation or similar effects.

All the compositions were tested for the EGF activity by ELISA and all the other ingredients were tested by the pharmacopeial methods or other appropriately validated methods which clearly confirm the activity.

EGF activity of the compositions was tested by means of proliferation of the 3T3 cell lines. Briefly, in this method, the known quantity of 3T3 cell were incubated with different quantities of standard EGF and formulated EGF and incubated at 37 degree C. for 5-8 days. Cell count was estimated and it was compared with the controls.

Results confirmed that the proliferation of cells treated with EGF was significantly higher as compared to the controls. Similarly SDS profile also showed the maintenance of the same profile for the entire period of study.

The scope of the combination is not limited just by the above range, but also to other combinations, which can still maintain the same functional activity of EGF known to those who are skilled in the art.

In the foregoing specification, specific embodiments of the present invention have been described. However, one of ordinary skill in the art appreciates that various modifications and changes can be made without departing from the scope of the present invention as set forth in the claims below. Accordingly, the specification and the examples are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the dependency of this application and all equivalents of those claims as issued.

What is claimed:

1. A composition comprising recombinant human epidermal growth factor present in a range of about 0.001% to about 0.9% (w/w); L-lysine hydrochloric acid present in the range of about 0.2% to about 0.5% (w/w) and mannitol present in the range of about 1% to about 10% (w/w) as stabilizers; sodium methyl paraben present in the range of about 0.016% to about 0.18% (w/w) and sodium propyl paraben present in the range of about 0.01% to about 0.02% (w/w) as preservatives; poly acrylic acid present in the range of about 0.25% to about 1% (w/w) as a thickening agent; water present in the range of about 50% to about 99.5% (w/v) as a carrier; triethanol amine present in an effective amount to maintain the pH of the composition between 6.3 to 6.4 as a pH regulating agent; glycerol present in the range of about 1% to about 2.5% (w/w) as a humectant; and a therapeutic agent present in a range of about 0.005% to about 0.5% (w/w).

2. The composition of claim 1, wherein the recombinant human epidermal growth factor is in a topical formulation in the form of gel, spray, ointment, cream and lotion, in oral formulation in the form of tablet and capsule, or in parenteral formulation in the form of injections.

3. The composition of claim 1, wherein the therapeutic agent is an antiinfective agent silver sulphadiazine present in a range of about 0.005% to about 0.5% (w/w).

4. The composition of claim 1, wherein the therapeutic agent is a recombinant antibiotic lysostaphin present in the range of about 0.01% to about 0.1% (w/w).

5. The composition of claim 1, wherein the therapeutic agent is hyaluronic acid present in the range of about 0.05% to about 5% (w/w).

6. The composition of claim 1, wherein the therapeutic agent is Granulocyte Macrophage Colony Stimulating Factor (GM-CSF) present in the range of about 0.001% to 0.005% (w/w).

7. The composition of claim 1, wherein the therapeutic agent is Platelet Derived Growth Factor present in the range of about 0.005% to about 0.01% (w/w).

8. The composition of claim 1, wherein the therapeutic agent is an immune modulator beta 1,3-D-glucan present in the range of about 0.5% to about 2% (w/w).

9. The composition of claim 1, wherein the therapeutic agent is present in a combination with a vaso constrictor hydrocortisone acetate present in the range of about 0.215% (w/w), zinc oxide present in the range of about 0.015% to about 5% (w/w), lindocaine present in the range of about 2% to 3% (w/w), and allantoin present in the range of about 0.4% to about 1.5% (w/w).

10. The composition of claim 1, wherein the therapeutic agent is present in a combination of natural product(s) consisting of aloevera; turmeric; sandalwood; and honey.

11. The composition of claim 1, wherein the therapeutic agent is present in a combination of natural product(s) consisting of aloevera; Vitamin E and Vitamin C.

12. The composition of claim 1, wherein the therapeutic agent is protein free blood extract, present in the range of about 0.015% to 0.02% (w/w).

13. The composition of claim 1, wherein the therapeutic agent is present in combination of zinc oxide present in the range of about 0.015% to about 5% (w/w), salicylic acid present in the range of about 1% to about 5% (w/w) and clobetasol propionate present in the range of about 0.1% to about 1% (w/w).

* * * * *